United States Patent
Tsuji et al.

(10) Patent No.: US 7,381,829 B2
(45) Date of Patent: Jun. 3, 2008

(54) METHOD FOR PRODUCING PROPYLENE OXIDE

(75) Inventors: Junpei Tsuji, Chiba (JP); Masaru Ishino, Sodegaura (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 55 days.

(21) Appl. No.: 10/572,876

(22) PCT Filed: Sep. 15, 2004

(86) PCT No.: PCT/JP2004/013880

§ 371 (c)(1),
(2), (4) Date: Mar. 22, 2006

(87) PCT Pub. No.: WO2005/030741

PCT Pub. Date: Apr. 7, 2005

(65) Prior Publication Data

US 2006/0293531 A1    Dec. 28, 2006

(30) Foreign Application Priority Data

Sep. 26, 2003 (JP) ............................. 2003-335327

(51) Int. Cl.
*C07C 301/14* (2006.01)
*C07C 301/19* (2006.01)
(52) U.S. Cl. ...................................... 549/525; 549/529
(58) Field of Classification Search ................ 549/525
See application file for complete search history.

(56) References Cited

U.S. PATENT DOCUMENTS

| 3,526,674 A | | 9/1970 | Becker et al. |
| 4,075,254 A | * | 2/1978 | Boodman et al. ............ 260/667 |
| 4,257,877 A | | 3/1981 | Mahendroo |
| 5,693,193 A | | 12/1997 | DeGuchi et al. |
| 5,723,637 A | * | 3/1998 | Tsuji et al. .................. 549/529 |
| 6,160,137 A | * | 12/2000 | Tsuji et al. .................. 549/523 |
| 2003/0032822 A1 | * | 2/2003 | Tsuji et al. .................. 549/529 |

FOREIGN PATENT DOCUMENTS

| CS | 140743 | 3/1971 |
| JP | 53-82703 A | 7/1978 |
| JP | 56-55318 A | 5/1981 |
| JP | 8-104682 A | 4/1996 |
| JP | 2001-270880 A | 10/2001 |
| WO | WO 2004/058667 A1 | 7/2004 |
| WO | WO 2004/060838 A1 | 7/2004 |

* cited by examiner

*Primary Examiner*—Sikarl A. Witherspoon
(74) *Attorney, Agent, or Firm*—Sughrue Mion, PLLC

(57) ABSTRACT

A process for producing propylene oxide, which comprises the following steps:
  oxidation step: a step of obtaining cumene hydroperoxide by oxidizing cumene;
  epoxidation step: a step of obtaining propylene oxide and cumyl alcohol by reacting cumene hydroperoxide obtained in the oxidation step with propylene; and
  converting step: a step of converting cumyl alcohol obtained in the epoxidation step into cumene in the presence of a solid catalyst and recycling said cumene to the oxidation step,
  wherein a concentration of methylbenzyl alcohol in a liquid containing cumene recycled to the oxidation step, is 1% by weight or less.

3 Claims, No Drawings

METHOD FOR PRODUCING PROPYLENE OXIDE

TECHNICAL FIELD

The present invention relates to a process for producing propylene oxide.

BACKGROUND ART

Though a process in which propylene can be converted into propylene oxide using cumene hydroperoxide obtained from cumene as an oxygen carrier, and cumene can be used repeatedly, is disclosed in Czechoslovakia patent CS140743 and JP2001-270880 A, it is insufficient in an industrial operation from the viewpoint of productivity.

DISCLOSURE OF THE INVENTION

An object of the invention is to provide a process for producing propylene in which propylene is converted into propylene oxide using cumene hydroperoxide obtained from cumene as an oxygen carrier, the cumene can be used repeatedly, and further oxidation can be efficiently carried out thereby being able to efficiently produce propylene oxide.

Namely, the present invention relates to a process for producing propylene oxide, which comprises the following steps:

oxidation step: a step of obtaining cumene hydroperoxide by oxidizing cumene;

epoxidation step: a step of obtaining propylene oxide and cumyl alcohol by reacting cumene hydroperoxide obtained in the oxidation step with propylene; and converting step: a step of converting cumyl alcohol obtained in the epoxidation step into cumene and recycling said cumene to the oxidation step, wherein a concentration of methylbenzyl alcohol in a liquid containing cumene recycled to the oxidation step, is 1% by weight or less.

BEST MODE FOR CARRYING OUT THE INVENTION

The oxidation step is a step for obtaining cumene hydroperoxide by oxidizing cumene. The oxidation of cumene is usually conducted by auto-oxidation using an oxygen-containing gas such as air or oxygen-concentrated air. This oxidation may be conducted without use of an additive, and an additive such as an alkali may be used. The reaction temperature is usually from 50 to 200° C., and the reaction pressure is usually between atmospheric pressure and 5 MPa. In the oxidation method in which the additive is used, an alkali metal compound such as NaOH or KOH, an alkaline earth metal compound, or alkali metal carbonate such as $Na_2CO_3$ or $NaHCO_3$, ammonia, $(NH_4)_2CO_3$, an alkali metal ammonium carbonate or the like, is used as an alkali reagent.

The epoxidation step is a step for obtaining propylene oxide and cumyl alcohol by reacting cumene hydroperoxide obtained in the oxidation step with propylene. The epoxidation step is preferably conducted in the presence of an epoxidation catalyst, particularly a catalyst containing titanium-containing silicon oxide from the viewpoint of obtaining propylene oxide under high yield and high selectivity. As the catalyst, so-called Ti-silica catalysts containing Ti chemically bonded to silicon oxide, are preferable. For example, a catalyst prepared by supporting a Ti compound on a silica carrier, a catalyst prepared by combining a Ti compound with silicon oxide by a co-precipitation method or sol gel method, zeolite compounds containing Ti, and the like, can be listed.

Cumene hydroperoxide used as a raw material in the epoxidation step, may be a dilute or dense purified material or non-purified material.

The epoxidation is conducted by contacting propylene and cumene hydroperoxide with the catalyst. The reaction is carried out in a liquid phase using a solvent. The solvent should be liquid under a temperature and a pressure during the reaction, and substantially inert to reactants and products. The solvent may be a substance present in a hydroperoxide solution to be used. For example, when cumene hydroperoxide is a mixture with cumene which is a raw material thereof, the cumene can be used as a substitute of a solvent without particularly adding a solvent.

The epoxidation temperature is usually from 0 to 200° C., and preferably from 25 to 200° C. The pressure may be a pressure sufficient to keep the reaction mixture in a liquid condition. In general, the pressure is advantageously from 100 to 10,000 kPa.

The epoxidation can be advantageously conducted using a catalyst in the form of a slurry or fixed bed. In the case of a large-scale industrial operation, a fixed bed is preferably used. In addition, the epoxidation can be conducted by a batch-wise method, a semi-continuous method or a continuous method.

When a liquid containing a raw material for reaction is passed through a fixed bed, the catalyst is not contained at all or substantially in a liquid mixture drawn out from the reaction zone.

The conversion step is a step of converting cumyl alcohol obtained in the epoxidation into cumene and recycling the cumene to the oxidation step as a raw material. As a method for converting cumyl alcohol into cumene, a method of first dehydrating cumyl alcohol to obtain α-methyl styrene and then hydrogenating α-methyl styrene to convert into cumene, and a method of subjecting cumyl alcohol to hydrogenolysis to directly convert into cumene, can be illustrated. From viewpoints of catalyst life and yield, a combination of the dehydration step and hydrogenation step is preferably carried out.

A case in which the conversion step is composed of the dehydration step and hydrogenation step, is explained below.

It is preferable to separate propylene oxide obtained by the epoxidation from cumyl alcohol before the dehydration step from the viewpoint of obtaining high yield of propylene oxide.

As a separation method, distillation can be used.

A catalyst used in the dehydration includes acids such as sulfuric acid, phosphoric acid and p-toluene sulfonic acid and metal oxides such as activated alumina, titania, zirconia, silica-alumina and zeolites, and activated alumina is preferable from viewpoints of separation from the reaction mixture, catalyst life, selectivity, etc.

The dehydration is usually conducted by contacting cumyl alcohol with the dehydration catalyst, but, in the present invention, hydrogen may be also to the catalyst to conduct hydrogenation subsequent to the dehydration. The reaction can be conducted in a liquid phase using a solvent. The solvent should be substantially inert to reactants and products. The solvent may be a substance present in a cumyl alcohol solution to be used. For example, when cumyl alcohol is a mixture with cumene as a product, it is possible to use cumene as a substitute without adding a solvent in particular. The dehydration temperature is usually 50 to 450° C., preferably 150 to 300° C. In usual, the pressure is advantageously 10 to 10,000 kPa. The dehydration can be advantageously conducted by using a catalyst in a slurry form or fixed-bed form.

The hydrogenation step is a step for converting into cumene by supplying α-methyl styrene obtained by the dehydration to a hydrogenation catalyst to hydrogenate α-methyl styrene and for recycling cumene to the oxidation step.

Though the hydrogenation catalyst includes catalysts containing a metal of Group 10 or 11 of the Periodic Table, and specifically, nickel, palladium, platinum and copper, palladium or copper are preferable from viewpoints of suppression of hydrogenation of the aromatic ring and high yield. As a copper catalyst, copper, Raney copper, copper/chromium, copper/zinc, copper/chromium/zinc, copper/silica, copper/alumina and the like are listed. As a palladium catalyst, palladium/alumina, palladium/silica, palladium/carbon and the like are listed. These catalysts can be used alone or in combination of two or more.

Though the hydrogenation is usually carried out by contacting α-methyl styrene and hydrogen with the catalyst, a part or the whole of water generated in the dehydration may be separated by oil-water separation or the like or may be supplied together with α-methyl styrene without separating to the hydrogenation catalyst for carrying out the hydrogenation subsequent to the dehydration.

Though the amount of hydrogen required in the reaction may be equimolar to α-methyl styrene, an excess amount of hydrogen is required because other components which consume hydrogen, are usually contained in the raw material.

As a molar ratio of hydrogen to α-methyl styrene, the range of 1 to 10 is usually applied because the reaction proceeds rapidly with increase of a partial pressure of hydrogen. The range is further preferably 1 to 5. The excess amount of hydrogen remained after the reaction can be also recycled after separated from the reaction mixture. The hydrogenation can be conducted in a liquid phase using a solvent or gas phase. The solvent must be substantially inert to the reactants and products. The solvent may be a substance existing in an α-methyl styrene solution to be used. For example, when α-methyl styrene is a mixture with cumene as a product, it is possible to use cumene as a substitute of the solvent without adding a solvent in particular. The hydrogenation temperature is usually 0 to 500° C., preferably 30 to 400° C. In usual, the pressure is advantageously 100 to 10,000 kPa.

As modes of the dehydration and hydrogenation, these reactions can be usually conducted by a continuous method using a catalyst in the form of a fix-bed. The dehydration and hydrogenation may be conducted using separate reactors or a single reactor. As a reactor used in the continuous method, there are an adiabatic reactor and an isothermal reactor, and the adiabatic reactor is preferable because the isothermal reactor requires an apparatus for removal of heat. In a case of single adiabatic reactor, the temperature lowers with progress of the reaction because the dehydration of cumyl alcohol is an endothermic reaction, and on the other hand, since the hydrogenation of α-methyl styrene is an exothermic reaction, the temperature rises with progress of the reaction. The outlet temperature becomes higher than the inlet temperature because the generated heat quantity is larger in total.

The reaction temperature and pressure are selected so that water contained in an α-methyl styrene solution after the dehydration, is not condensed. The reaction temperature is preferably 150 to 300° C., and the reaction pressure is preferably 100 to 2000 kPa. When the temperature is too low or the pressure is too high, water may be condensed at the outlet of the dehydration, leading to deterioration of the performance of the dehydration catalyst. Further, when the pressure is too high, it is also disadvantageous in the reaction equilibrium of dehydration. When the temperature is too high or the pressure is too low, it may become disadvantageous because the catalyst life is shortened by howling or the like caused by much generation of the gas phase part.

Though hydrogen can be supplied from any one of an inlet of a fixed bed and an inlet of the hydrogenation catalyst, it is preferable to supply from the inlet of the dehydration reactor in view of the activity of the dehydration catalyst. That is, vaporization of water produced through dehydration is promoted by bringing into constant existence of hydrogen in the dehydration zone and the equilibrium dehydration conversion rises, therefore, high conversion can be attained effectively compared to absence of hydrogen. Though water generated in the dehydration is passed through the hydrogenation catalyst, it is possible to operate at low cost without particularly setting up an apparatus for water removal as described above, by operating at the level not condensing water. Further, unreacted hydrogen in the outlet of the reactor can be recycled after gas-liquid separation operation.

Furthermore, at the time of the gas-liquid separation operation, it is possible to separate water generated in the dehydration from the reaction mixture. A part of the obtained reaction mixture (mainly cumene) can be recycled to the inlet of the reactor for use.

An amount of the dehydration catalyst used may be an amount enough to convert cumyl alcohol, and the conversion of cumyl alcohol is preferably 90% or more. An amount of the hydrogenation catalyst used may be an amount enough to convert α-methyl styrene into cumene, and the conversion of α-methyl styrene is preferably 98% or more.

Considering from a viewpoint of cost, the dehydration and hydrogenation catalysts are preferably packed in one fixed bed reactor without using multi stage reactors. Inside of the reactor may be partitioned into several beds or not. When the reactor is not partitioned, the dehydration catalyst and hydrogenation catalyst may be directly contacted each other or those may be partitioned with an inert packing.

A case of which the converting step is composed of hydrogenolysis, is explained below:

The hydrogenolysis step is a step for obtaining cumene by subjecting cumyl alcohol obtained in the epoxidation step to hydrogenolysis and for recycling the cumene to the oxidation step. In other words, cumene which has been used in the oxidation step is reproduced by the hydrogenolysis. The hydrogenolysis is carried out by contacting cumyl alcohol and hydrogen with a catalyst. As the catalyst, any catalyst having hydrogenation ability can be used. Though examples of the catalyst include metal-based catalysts of metals of Group 9 and 10 such as cobalt, nickel and palladium metal and metal-based catalysts of metals of Group 11 and 12 such as copper and zinc, copper-based catalysts are preferable from the viewpoint of suppression of by-products.

As the copper-based catalyst, copper, Raney copper, copper-chromium, copper-zinc, copper-chromium-zinc, copper-silica, copper-alumina and the like are listed.

The reaction can be conducted in a liquid phase using a solvent or a gas phase. The solvent should be substantially inert to the reactants and products. The solvent may be a substance existing in a cumyl alcohol solution to be used. For example, when cumyl alcohol is a mixture with cumene as a product, it is possible to use cumene as a substitute of the solvent without adding a solvent in particular.

Though the amount of hydrogen required in the hydrogenolysis may be equimolar to cumyl alcohol, an excess amount of hydrogen is required because other components which consume hydrogen, are usually contained in the raw material. Further, the molar ratio of hydrogen to cumyl alcohol is usually from 1 to 10 because the reaction proceeds rapidly with increase of a partial pressure of hydrogen. The ratio is further preferably from 1 to 5. The excess amount of hydrogen remained after the reaction may be recycled after separated from the reaction mixture. The hydrogenolysis temperature is usually 0 to 500° C., preferably 30 to 400° C. In usual, the pressure is advantageously 100 to 10,000 kPa. The hydrogenolysis can be advantageously carried out using a catalyst in the form of slurry or a fixed bed.

The present process can be conducted by a batch method, semi-continuous method or continuous method.

When a liquid or gas containing a raw material for reaction is passed through a fixed bed, the catalyst is not contained at all or substantially in a liquid mixture drawn out from the reaction zone.

In the present invention, it is required that a concentration of methylbenzyl alcohol contained in a liquid containing cumene after the oxidation step is 1% by weight or less, and 0.3% by weight or less is preferred. Herein, the liquid containing cumene means liquid cumene or a solution containing cumene when a solvent is contained.

Methyl benzyl is a compound produced by which acetophenone formed by thermal decomposition of cumene hydroperoxide in the oxidation and epoxidation steps, is hydrogenated in the converting step. Since methylbenzyl alcohol is a component accumulated in the reaction system, and the concentration increases with time when the recycle is continued, it can becomes an oxidation-inhibiting substance in addition to reduction of the reaction effective volume.

In the oxidation step inhibited, it is required to raise a reaction temperature or to prolong a reaction time for obtaining a desired cumene hydroperoxide. However, in both cases, by-products inhibiting the epoxidation are generated or an alcohol or a ketone consuming hydrogen in the hydrogenation step, is generated. Taking account of effective utilization of the reaction volume, suppression of reaction inhibition of the oxidation and epoxidation, and effective hydrogenation, the concentration of methylbenzyl alcohol in the liquid containing cumene to be recycled to the oxidation step must be controlled within the range of the present invention.

As methods for controlling the concentration of methylbenzyl within the range of the present invention, a method of removing a part or the whole of methylbenzyl alcohol outside the reaction system by distillation, extraction or the like, a method of converting into another compound, a method of decreasing the concentration using an adsorbent or the like, and the like, can be illustrated. A step for removing methylbenzyl alcohol outside the reaction system (herein-after, sometimes referred to as "methylbenzyl alcohol removal step") can be installed at least one place in the oxidation, epoxidation, dehydration and hydrogenation steps or between which the steps are connected, and can be usually carried out by distillation. As another method, the concentration of methylbenzyl alcohol can be effectively reduced by controlling reaction conditions in the hydrogenating step and hydrogenating most of acetophenone and methylbenzyl alcohol fed to the hydrogenation step to convert into ethylbenzene. Further, there can be also used a method of controlling production of methylbenzyl alcohol itself through selection of a hydrogenation catalyst not hydrogenating acetophenone. As a catalyst which hardly hydrogenates acetophenone, metal-based catalysts of metals of Group 9 and 10 such as cobalt, nickel and palladium, can be listed.

EXAMPLE

Example 1

Cumene recycled from a hydrogenation step was mixed with an aqueous solution of 1 wt. % of sodium carbonate in a volume ratio of 1 of the aqueous solution to 20 of cumene, and the mixture was reacted under atmospheric pressure and a temperature of 105° C. for of 1 hour supplying air.

A concentration of methylbenzyl alcohol in the recycled cumene was 0.02% by weight. A production rate of cumene hydroperoxide was 6.5% by weight per hour.

Example 2

A reaction operation was carried out in the same manner as in Example 1 except that the concentration of methylbenzyl alcohol in cumene recycled, was 0.2% by weight. The production rate of cumene hydroperoxide was 5.9% by weight per hour.

INDUSTRIAL APPLICABILITY

According to the present invention, there could be provided a process for producing propylene oxide, which can convert propylene into propylene oxide using cumene hydroperoxide obtained from cumene as an oxygen carrier, use repeatedly the cumene and further efficiently carry out oxidation thereby being able to efficiently produce propylene oxide.

The invention claimed is:

1. A process for producing propylene oxide, which comprises the following steps:
   oxidation step: a step of obtaining cumene hydroperoxide by oxidizing cumene;
   epoxidation step: a step of obtaining propylene oxide and cumyl alcohol by reacting cumene hydroperoxide obtained in the oxidation step with propylene; and
   converting step: a step of converting cumyl alcohol obtained in the epoxidation step into cumene in the presence of a solid catalyst and recycling said cumene to the oxidation step,
   wherein a concentration of methylbenzyl alcohol in a liquid containing cumene recycled to the oxidation step, is 1% by weight or less and
   wherein the process further comprises a step of removing methylbenzyl alcohol outside the reaction system at least one place in the steps or between which the steps are connected.

2. The process according to claim 1, wherein the conversion step comprises the following steps:
   dehydration step: a step of obtaining α-methyl styrene by dehydrating cumyl alcohol obtained in the epoxidation step in the presence of a dehydration catalyst; and
   hydrogenation step: a step of obtaining cumene by hydrogenating α-methyl styrene in the presence of a solid catalyst to obtain cumene, and recycling the cumene as a new material to the oxidation step.

3. The process according to claim 1, wherein the conversion step comprises the following step:
   hydrogenolysis step; a step of obtaining cumene by subjecting cumyl alcohol obtained in the epoxidation step to hydrogenolysis in the presence of a hydrogenolysis catalyst, and recycling the cumene to the oxidation step.

* * * * *